United States Patent [19]

Dubreuil et al.

[11] Patent Number: 4,645,571

[45] Date of Patent: Feb. 24, 1987

[54] METHOD AND APPARATUS FOR THE CONTINUOUS MONITORING OF SPECIFIC ELEMENTS IN MOLTEN SUBSTANCES CONTAINING SAME

[75] Inventors: Alain Dubreuil, Montreal; Arthur D. Pelton, Mount-Royal, both of Canada

[73] Assignee: La Corporation de l'Ecole Polytechnique, Montreal, Canada

[21] Appl. No.: 674,030

[22] Filed: Nov. 23, 1984

[51] Int. Cl.⁴ ............................................. G01N 27/30
[52] U.S. Cl. .................................... 204/1 T; 204/422; 204/433; 204/435
[58] Field of Search ................ 204/1 T, 1 A, 413, 421, 204/422, 435, 423, 433; 429/104

[56] References Cited

U.S. PATENT DOCUMENTS

| | | | |
|---|---|---|---|
| 3,468,780 | 9/1969 | Fischer | 204/422 |
| 3,676,319 | 7/1972 | Kirsten | 204/435 |
| 3,794,569 | 2/1974 | Kawai et al. | 204/1 T |
| 3,816,269 | 6/1974 | Wilder | 204/1 T |
| 3,980,543 | 9/1976 | Eckfeldt | 204/1 T X |
| 4,085,023 | 4/1978 | Fray | 204/422 |
| 4,166,021 | 8/1979 | Ross, Jr. et al. | 204/435 |
| 4,414,093 | 11/1983 | Redey et al. | 204/435 X |
| 4,428,770 | 1/1984 | Worrell et al. | 204/422 X |

Primary Examiner—John F. Niebling
Assistant Examiner—Nam X. Nguyen
Attorney, Agent, or Firm—Schwartz, Jeffery, Schwaab, Mack, Blumenthal & Evans

[57] ABSTRACT

The continuous monitoring of an element in a molten substance containing same is effected by monitoring the electromotive force generated between a first electrode in contact with the substance and a second electrode in contact with a reference material which is separated from the substance by a solid electrolyte. The reference material comprises a metal and at least one salt selected from the group consisting of (a) a combined salt of the metal and a monovalent metal, (b) a mixture of a first salt of the metal and a second salt of the monovalent metal, the first and second salts having a common anion, (c) a mixture of the first salt and the combined salt, and (d) a mixture of the second salt and the combined salt, the at least one salt being present in the form of a slurry containing a liquid phase in equilibrium with a solid phase, the liquid phase containing the metal and monovalent metal in ionic form and the solid phase containing the first salt, second salt or combined salt. The use of such a reference material enables one to obtain reproducible results and to minimize the polarizability of the electrodes.

38 Claims, 3 Drawing Figures

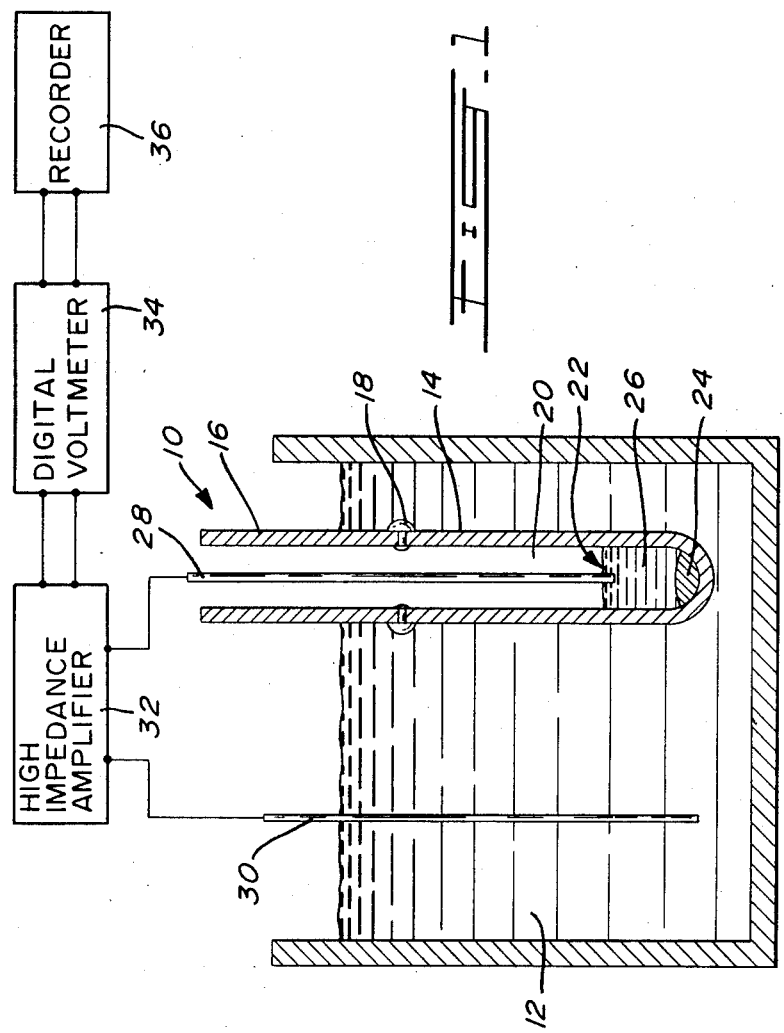

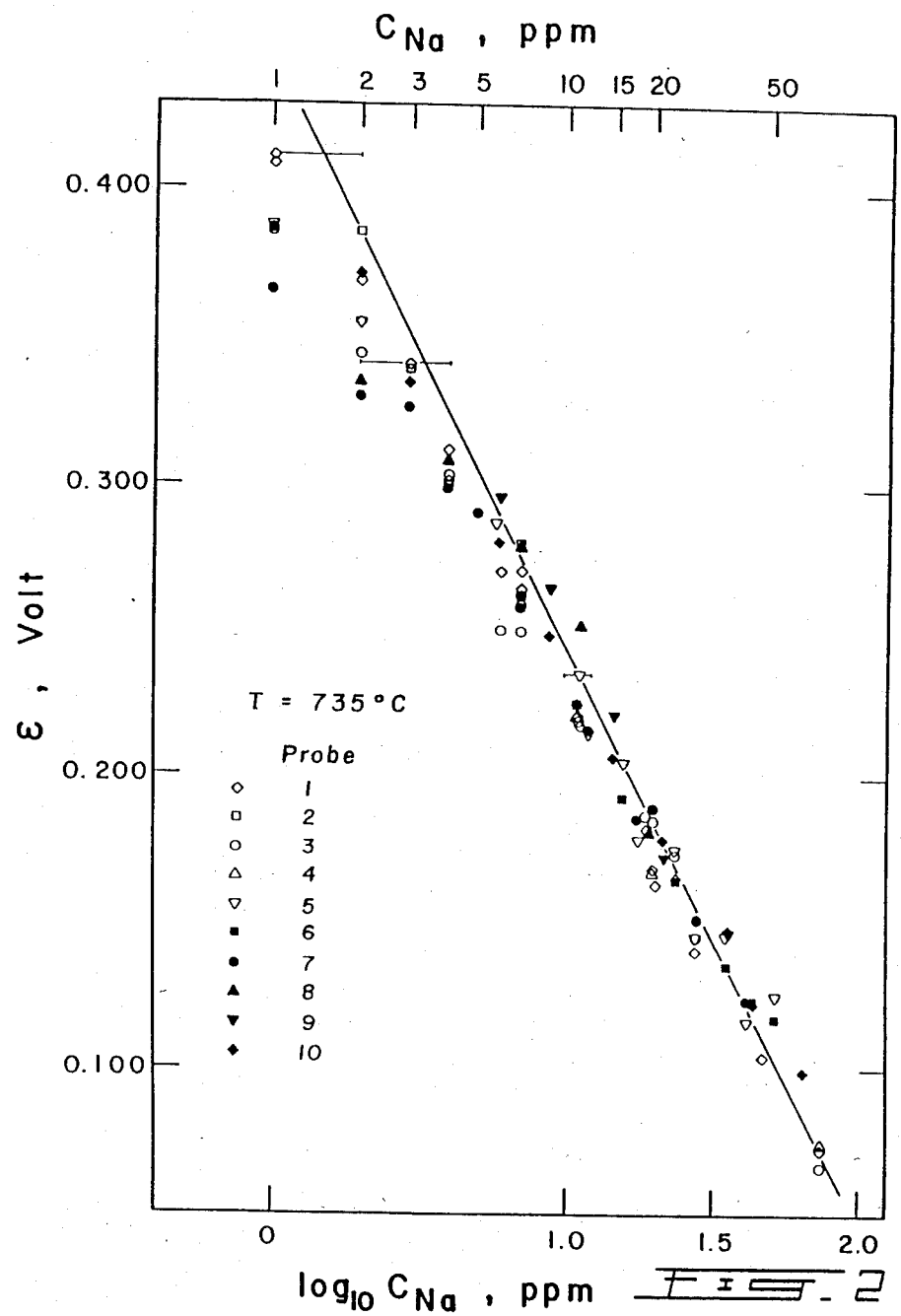

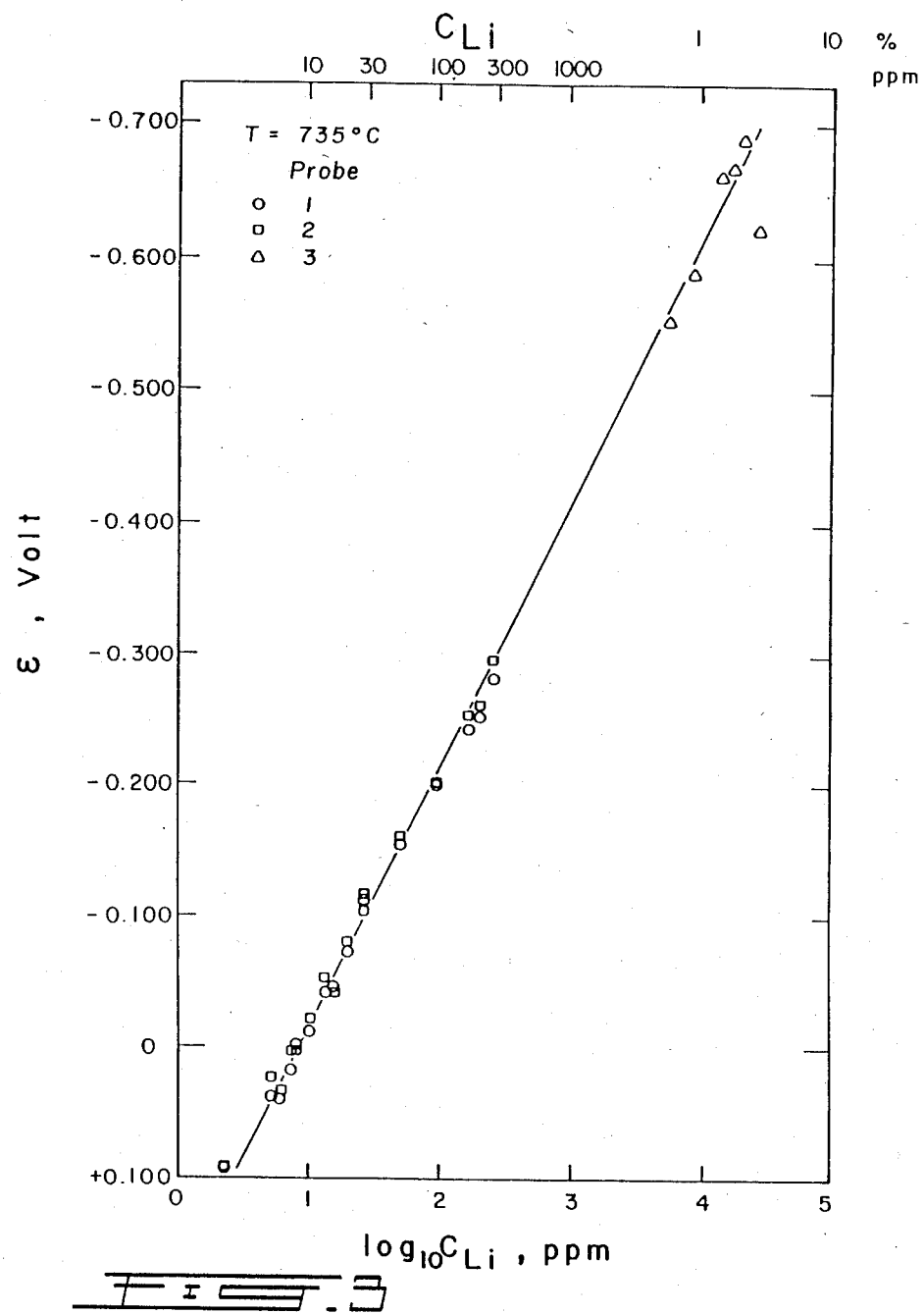

METHOD AND APPARATUS FOR THE CONTINUOUS MONITORING OF SPECIFIC ELEMENTS IN MOLTEN SUBSTANCES CONTAINING SAME

BACKGROUND OF THE INVENTION

The present invention relates to improvements in the continuous monitoring of an element in a molten substance containing same, by monitoring the electromotive force (emf) generated between the substance and a reference material. More particularly, the invention is concerned with an improved electrochemical probe for use as reference electrode in carrying out such monitoring.

During the refining of aluminum, the sodium content of molten aluminum must be reduced to the order of a few parts per million, particularly if thin sheets are to be rolled. At present, the Na content is monitored by spectroscopic analysis of samples. It would be advantageous to develop a so-called "sodium-probe" suitable for industrial application and which could be placed in the molten aluminum to give an immediate and continuous reading of the Na content. Such a probe would also be useful in determining the Na content of molten Al-Si alloys to which Na in concentrations of the order of 100 ppm has been added as a structural modifier.

Similarly, lithium must also be removed from molten Al during refining, and an analogous "Li-probe" for the continuous monitoring of Li contents in the ppm range would be an asset. Such a probe would also be very useful in measuring the Li content of molten Al-Li alloys in which the Li concentration is of the order to a few weight %.

Fray has already proposed in British Pat. No. 1,470,558 a solid electrolyte probe based on $\beta$-alumina for measuring the Na concentration in molten Al. The reference material used by Fray is solid and comprises a mixture of $\alpha$-alumina and $\beta$-alumina in equilibrium with the atmospheric air. Although this system responds to the presence of Na in molten Al, the experimental results obtained do not agree with Nernst's Law since the sodium concentration varies in linear manner with the emf generated between the electrodes. It would appear that since the equilibrium reaction occurs in solid phase, the speed of reaction is slow so that the reference electrode potential is unstable. The electrodes were also found to be quite polarizable and very sensitive to humidity absorbed on the electrolyte surface. As a result, such a Na-probe lacks precision and reproducibility.

Fray later proposed in British Pat. No. 1,602,564 an improved version of the above Na-probe, consisting of an airtight probe in which the reference material comprises a mixture of $\alpha$-alumina, $\beta$-alumina and a mixture of a metal and metal oxide such as a $Cu/CuO_2$, $Cr/Cr_2O_3$ or $Ni/NiO$ mixture which provides a fixed oxygen potential within the sealed probe. However, the experimental results obtained still showed polarizability of the electrodes and did not have a reproducibility sufficient for enabling such probes to be useful in the metallurgical industry.

SUMMARY OF THE INVENTION

It is therefore an object of this invention to overcome the above drawbacks and to provide a method and apparatus permitting the continuous monitoring of an element in a substance containing same, with a precision and reproducibility sufficient for practical industrial applications.

According to one aspect of the invention, there is provided in a method for the continuous monitoring of an element in a molten substance containing same by monitoring the electromotive force generated between the substance and a reference material separated from the substance by a solid electrolyte, the improvement wherein the reference material comprises a metal and at least one salt selected from the group consisting of (a) a combined salt of the metal and a monovalent metal, (b) a mixture of a first salt of the metal and a second salt of the monovalent metal, the first and second salts having a common anion, (c) a mixture of the first salt and the combined salt, and (d) a mixture of the second salt and the combined salt. The at least one salt is present in the form of a slurry containing a liquid phase in equilibrium with a solid phase, the liquid phase containing the metal and monovalent metal in ionic form and the solid phase containing the first salt, second salt or combined salt.

According to another aspect of the invention, there is also provided a high temperature electrochemical probe for use as reference electrode in the continuous monitoring of an element in a molten substance containing same, which comprises a solid electrolyte defining a reference electrode compartment, a reference material contained in the reference electrode compartment, and an electrode in contact with the reference material, the reference material being as defined above and adapted to form the aforesaid slurry at the operating temperature of the probe.

The solid electrolyte generally used comprises $\beta$-alumina which can be manufactured in the form of closed-end vacuum-tight tubes. This configuration permits the reference electrode compartment inside the tube to be separated from the other electrode compartment outside. $\beta$-alumina is a ceramic which is stable at high temperatures and which is resistant to chemical attack in molten metal and salt environments. It is an ionic conductor in which charge transport occurs via monovalent cations such as $Na^+$, $K^+$, $Li^+$, $Ag^+$, $Rb^+$, $Cs^+$, etc. Sodium $\beta$-alumina is particularly preferred due to the high mobility of the $Na^+$ ions.

The components of the reference material, on the other hand, are selected to ensure the presence of a liquid phase in equilibrium with a solid phase at the operating temperature of the probe. The presence of this liquid phase has been found to substantially improve the equilibrium reaction, thereby ensuring that thermodynamic equilibrium between all phases is fully obtained and minimizing the polarizability of the reference electrode.

Thus, if $\beta$-alumina is used in a galvanic cell as a solid electrolyte separating two electrode compartments in which the activities of the element X to be monitored and of the reference element Y are $a_X{}^I$ and $a_Y{}^{II}$:

$$\left. \begin{array}{c} X \\ \text{at activity } a_X^I \end{array} \right| \beta\text{-alumina} \left| \begin{array}{c} Y \\ \text{at activity } a_Y^{II} \text{ (reference)} \end{array} \right. \qquad (I)$$

then the cell potential $E$ is given by the following equation:

$$E = E' + \frac{RT}{F} \ln \frac{k\, a_Y^{II}}{a_X^I}$$

where T is the temperature in °K., R is the gas constant, F is Faraday's constant, E' and k are constants for a given temperature and are function of the elements X and Y which are monovalent metals. If $a_Y^{II}$ in the reference electrode compartment is fixed, equation (I) can be rewritten as follows:

$$E = E° - \frac{RT}{F} \ln a_X^I \quad \text{(II)}$$

where E° is a constant depending upon the reference material used and is function of $a_Y^{II}$ for a given temperature. The cell can therefore be used to measure $a_X^I$ in the other electrode compartment.

Preferably, the reference element Y is the same as the element X to be monitored. Thus, for example, in the case of a Na-probe, the reference material used will be such as to fix a reference sodium activity.

Where the electrochemical probe of the invention is to be used as Na-probe, the reference material preferably comprises Al, $Na_3AlF_6$, NaF and NaCl. It should be noted that the sodium chloride does not take part in the electrochemical reaction and is added solely for the purpose of providing the necessary liquid phase at the operating temperature of the probe, which is usually in the range of 700°–800° C. In this case, the equilibrium in the reference electrode compartment is among liquid Al, solid $Na_3AlF_6$, solid NaF and a liquid phase consisting of NaCl saturated in both NaF and $Na_3AlF_6$. Such a reference material may comprise, for example, the following components:

Al: about 5–40%, preferably about 20% by weight,
$Na_3AlF_6$: about 2–82%, preferably about 35% by weight,
NaF: about 3–84%, preferably about 23% by weight,
NaCl: about 5–47%, preferably about 25% by weight.

A particularly preferred reference material comprises about 20% Al, about 38% $Na_3AlF_6$, about 18% NaF and about 24% NaCl, expressed in percentage by weight.

In the case of a Li-probe, the reference activity of Li may be fixed analogously by the equilibrium among Al, $Li_3AlF_6$ and LiF. Since the eutectic between LiF and $Li_3AlF_6$ occurs at 708° C. (compared to 888° C. for the $NaF-Na_3AlF_6$ eutectic), a liquid phase is already present in the temperature range of about 710°–770° C. at which the probe is to be used. Hence, no chloride addition is necessary. In this case, the equilibrium in the reference electrode compartment is among liquid Al, solid $Li_3AlF_6$ and a liquid phase of LiF saturated in $Li_3AlF_6$. The LiF and $Li_3AlF_6$ may be used in a weight ratio LiF:$Li_3AlF_6$ ranging from about 11:24 to about 5:32, preferably about 3:17. The LiF:$Li_3AlF_6$ ratio may also range from about 20:9 to about 11:23, preferably about 19:10; in this case, the equilibrium is among liquid Al, solid LiF and a liquid phase consisting of $Li_3AlF_6$ saturated in LiF and the probe can be used at a temperature of up to about 820° C. A preferred composition comprises about 20% Al, about 68% $Li_3AlF_6$ and about 12% LiF, expressed in percentage by weight. It is also possible to replace the LiF by $AlF_3$ for an operating temperature range of about 710° to about 770° C.; the $AlF_3$ and $Li_3AlF_6$ may thus be used in a weight ratio $AlF_3$:$Li_3AlF_6$ ranging from about 6:38 to about 12:35, preferably 7:37.

The electrochemical probes of the invention may be used in the aluminum industry for the continuous monitoring of the Na content of molten Al in the range of 1 ppm to saturated and of the Li content of molten Al in the range of 1 ppm to 3 weight %. The probes are robust and thermal-shock resistant and may be left in the Al bath for several hours.

A further application of the probes according to the present invention in the aluminum industry is in the continuous monitoring of the ratio $NaF/AlF_3$ in the cryolite bath of a Hall Cell. Since the bath is in equilibrium with molten Al, the ratio uniquely determines a sodium activity which may be measured by the probe. In this case, the reference material may comprise Al and $Na_3AlF_6$ in admixture with NaF or $Na_5Al_3F_{14}$. As this "ratio-probe" is generally used at a temperature of about 950° C., and where the reference material consists of Al, $Na_3AlF_6$ and NaF, the equilibrium in the reference electrode compartment is among liquid Al, solid $Na_3AlF_6$ and a liquid phase of NaF saturated in $Na_3AlF_6$. The NaF and $Na_3AlF_6$ may be used in a weight ratio NaF:$Na_3AlF_6$ ranging from about 17:31 to about 2:50, preferably about 5:46. On the other hand, when Al, $Na_3AlF_6$ and $Na_5Al_3F_{14}$ are used as reference material, the equilibrium is among liquid Al, solid $Na_3AlF_6$ and a liquid phase of $Na_5Al_3F_{14}$ saturated in $Na_3AlF_6$; in this case, the $Na_5Al_3F_{14}$ and $Na_3AlF_6$ may be used in a weight ratio ranging from about 9:44 to about 37:19, preferably about 18:36.

BRIEF DESCRIPTION OF THE DRAWINGS

Further features and advantages of the invention will become more readily apparent from the following description of preferred embodiments thereof as illustrated by way of examples in the accompanying drawings, in which:

FIG. 1 is a schematic sectional view illustrating how an electrochemical probe according to the invention can be used for continuously monitoring an element in a molten substance containing same;

FIG. 2 is a diagram showing the results obtained with a Na-probe according to the invention; and FIG. 3 is another diagram showing the results obtained with a Li-probe according to the invention.

DESCRIPTION OF PREFERRED EMBODIMENTS

Referring first to FIG. 1, there is illustrated a high temperature electrochemical probe 10 for the continuous monitoring of an element contained in a molten substance 12. The probe 10 comprises a sodium β-alumina tube 14 which is closed at one end and connected at the other end to an alumina extension tube 16 by means of a ceramic cement 18 such as COTRONIX 940 (trademark). The tube 14 which has the approximate dimensions: 12 mm O.D., 9 mm I.D., 70 mm long is helium-tight, of 98% theoretical density, with a small uniform grain size, and may be fabricated from ALCOA XB2 (trademark) β-alumina powder.

The tube 14 defines a reference electrode compartment 20 which contains a reference material 22. The reference material 22 comprises a metal 24 which is generally liquid at the operating temperature of the probe as well as a slurry 26 containing a liquid phase in equilibrium with a solid phase. As mentioned previously, the slurry includes at least one salt selected from the group consisting of (a) a combined salt of the metal and a monovalent metal, (b) a mixture of a first salt of the metal and a second salt of the monovalent metal, the first and second salts having a common anion, (c) a mixture of the first salt and the combined salt, and (d) a mixture of the second salt and the combined salt, the liquid phase containing the metal and monovalent metal in ionic form and the solid phase containing the first salt, second salt or combined salt.

Electrical contact is achieved via a first stainless steel electrode 28 in contact with the reference material 22 and a second stainless steel electrode 30 in contact with the molten substance 12. The electromotive force generated between the two electrodes 28 and 30 is monitored by means of a high impedance amplifier 32 connected to a digital voltmeter which in turn is connected to a recorder 36.

A Na-probe such as that represented by reference numeral 10 was made using as reference material 22 a mixture comprising about 38% $Na_3AlF_6$, about 18% NaF and about 24% NaCl together with about 20% Al, expressed in percentage by weight. The slurry 26 thus consisted of a solid phase containing $Na_3AlF_6$ and NaF and of a liquid phase containing NaCl saturated in both NaF and $Na_3AlF_6$.

Measurements were performed with approximately 50 kg baths of commercial (99.6%) aluminium, to which was added sodium. After the sodium addition, the probe emf was followed during the approximately 5 hours required for the Na content to decrease by evaporation from approximately 100 ppm to 1 ppm. Samples were also taken periodically from the vicinity of the tip of the probe and were analyzed by optical emission spectroscopy. A standard sampling technique using a spoon was employed. Disc-shaped samples of 5.5 cm diameter were cast in moulds. The tips of the probes were approximately 20 cm below the melt surface. Ten probes having the same reference material were tested. Most probes remained in the bath for 10 hours during 2 cycles of Na addition and evaporation. When the probes were polarized by short-circuiting, the emf returned to its former value with 2 minutes.

The results obtained with the 10 Na-probes are reported in FIG. 2. The temperature varied over the range 710° to 750° during the measurements. The results in FIG. 2 have been normalized to 735° C. This entailed a correction of never more than 20 mV. Error bars of ±1 ppm are shown at three locations in FIG. 2 (the spectroscopic analyses were only reported to the nearest ppm).

The straight line drawn in FIG. 2 is the theoretical line calculated from thermodynamic data. It is not a least-squares regression line. At the lowest concentrations in FIG. 2, deviations of 1 to 1.5 ppm from the theoretical line are observed. Although this is approximately the precision of the spectroscopic analyses, the fact that the readings are nearly all systematically on the low side could be the result of sodium losses during sampling.

As it is apparent, the experimental results are not only reproducible but also in agreement with Nernst's Law, that is, the relationship between $\log_{10}C_{Na}$ and the emf is linear.

An analogous Li-probe 10 was also made using as reference material 22 a mixture comprising about 68% $Li_3AlF_6$ and about 12% LiF together with about 20% Al, expressed in percentage by weight. The slurry 26 thus consisted of a solid phase containing $Li_3AlF_6$ and of a liquid phase containing LiF saturated in $Li_3AlF_6$.

Measurements were carried out with 2 Li-probes having the same reference material in the composition range from 2 to 300 ppm Li in an Al bath of approximately 0.5 kg. After the lithium addition, the probe emf was followed during the approximately 4 hours required for the Li content to decrease from 300 to 2 ppm.

Samples were taken in quartz tubes and were analyzed by atomic absorption spectroscopy. Each probe remained in the bath for 8 hours during 2 cycles of Li addition and evaporation.

For Li contents in the range 0.5 to 7 weight %, measurements were made with a third Li-probe in a 50 kg bath of Al. Li additions were made periodically. After each addition, the probe emf was measured and a sample was taken for spectroscopic analysis. The entire run lasted 4 hours.

The results obtained with the 3 Li-probes as shown in FIG. 3 were normalized to 735° C. Since the actual temperature varied only over the range 730° to 745° C., this correction was never greater than 8 mV.

The line shown in FIG. 3 has the "Nernst slope", −(RT/F), but has been drawn to pass through the measured points. The line calculated from thermodynamic data is parallel to this line but displaced 92 mV lower. This corresponds to 8.9 kJ which is within the error limits of the thermodynamic literature data.

In the case of the Li-probe, the deviation of approximately 92 mV from the line calculated from the thermodynamic data is within the error limits of the latter as discussed above. Part of this deviation could also be due to a junction potential arising from the fact that sodium-beta-alumina rather than lithium-beta-alumina was used as solid electrolyte. However, this explanation would require that the junction potential be virtually constant for Li contents varying by over 4 orders of magnitude. In any case, the fact that the experimental line has the Nernst slope, −(RT/F), over 4 orders of magnitude in concentration argues strongly in favour of the reversibility of the cell. FIG. 3 also shows that the results are reproducible.

We claim:

1. In a method for the continuous monitoring over a predetermined temperature range of a monovalent metal in a molten substance containing same by monitoring the electromotive force generated between the substance and a reference material separated from the substance by a solid electrolyte, the improvement wherein said reference material comprises a metal in liquid state and a salt component selected from the group consisting of (a) a combined salt of said metal of said reference material and a further monovalent metal, (b) a mixture of a first salt of said metal of said reference material and a second salt of said further monovalent metal, said first and second salts having a common anion, (c) a mixture of said first salt and said combined salt, and (d) a mixture of said second salt and said combined salt, said salt component being present in the form of a slurry containing a liquid phase in equilibrium with a solid phase over a predetermined temperature range, said liquid phase containing said metal of said reference material and said further monovalent metal in ionic form and said solid phase containing said first salt, second salt or combined salt, said metal in liquid state and said solid and liquid phases of said slurry providing a three-phase equilibrium fixing an activity of said further monovalent metal.

2. A method according to claim 1, wherein a first electrolytically inert electrode is contacted with said substance and a second electrolytically inert electrode is contacted with said reference material, and the electromotive force generated between the two electrodes is monitored.

3. A method according to claim 1, wherein said solid electrolyte comprises a β-alumina containing a monovalent cation as ionic conductor.

4. A method according to claim 3, for the continuous monitoring of sodium in molten aluminum or alloy thereof, wherein said reference material comprises Al, Na$_3$AlF$_6$, NaF and NaCl.

5. A method according to claim 3, for the continuous monitoring of lithium in molten aluminum or alloy thereof, wherein said reference material comprises Al, Li$_3$AlF$_6$ and LiF.

6. A method according to claim 5, wherein said β-alumina is sodium β-alumina.

7. A method according to claim 3, for the continuous monitoring of lithium in molten aluminum or alloy thereof, wherein said reference material comprises Al, Li$_3$AlF$_6$ and AlF$_3$.

8. A method according to claim 7, wherein said β-alumina is sodium β-alumina.

9. A method according to claim 3, for the continuous monitoring of a NaF/AlF$_3$ ratio in a molten cryolite bath in equilibrium with molten aluminum, wherein said reference material comprises Al, Na$_3$AlF$_6$ and NaF.

10. A method according to claim 3, for the continuous monitoring of a NaF/AlF$_3$ ratio in a molten cryolite bath in equilibrium with molten aluminum, wherein said reference material comprises Al, Na$_3$AlF$_6$ and Na$_5$Al$_3$F$_{14}$.

11. A method according to claim 1, wherein said monovalent metal in said molten substance and said further monovalent metal are identical.

12. A high temperature electrochemical probe for use as a reference electrode in the continuous monitoring over a predetermined temperature range of a monovalent metal in a molten substance containing same, which comprises a solid electrolyte defining a reference electrode compartment, a reference material contained in said reference electrode compartment, and an electrolytically inert electrode in contact with said reference material, said reference material comprising a metal and a salt component selected from the group consisting of (a) a combined salt of said metal of said reference material and a further monovalent metal, (b) a mixture of a first salt of said metal of said reference material and a second salt of said further monovalent metal, said first and second salts having a common anion, (c) a mixture of said first salt and said combined salt, and (d) a mixture of said second salt and said combined salt, wherein said metal of said reference material is in liquid state and said salt component is present in the form of a slurry containing a liquid phase in equilibrium with a solid phase over said predetermined temperature range, said liquid phase containing said metal of said reference material and said further monovalent metal in ionic form and said solid phase containing said first salt, second salt or combined salt, said metal in liquid state and said solid and liquid phases of said slurry providing a three-phase equilibrium fixing an activity of said further monovalent metal.

13. An electrochemical probe according to claim 12, wherein said solid electrolyte comprises a β-alumina tube closed at one end, said β-alumina containing a monovalent cation as ionic conductor.

14. An electrochemical probe according to claim 13, for the continuous monitoring of sodium at temperatures of about 700° to about 800° C., wherein said reference material comprises Al, Na$_3$AlF$_6$, NaF and NaCl.

15. An electrochemical probe according to claim 14, wherein said reference material comprises about 5–40% Al, about 2–82% Na$_3$AlF$_6$, about 3–84% NaF and about 5–47% NaCl, expressed in percentage by weight.

16. An electrochemical probe according to claim 15, wherein said Al is present in an amount of about 20% by weight.

17. An electrochemical probe according to claim 15, wherein said Na$_3$AlF$_6$ is present in an amount of about 32% by weight.

18. An electrochemical probe according to claim 15, wherein said NaF is present in an amount of about 23% by weight.

19. An electrochemical probe according to claim 15, wherein said NaCl is present in an amount of about 25% by weight.

20. An electrochemical probe according to claim 15, wherein said reference material comprises about 20% Al, about 38% Na$_3$AlF$_6$, about 18% NaF and about 24% NaCl.

21. An electrochemical probe according to claim 13, for the continuous monitoring of lithium at temperatures of about 710° to about 820° C., wherein said reference material comprises Al, Li$_3$AlF$_6$ and LiF.

22. An electrochemical probe according to claim 21, wherein said β-alumina is sodium β-alumina.

23. An electrochemical probe according to claim 21, for the continuous monitoring of lithium at temperatures of about 710° to about 770° C., wherein said LiF and Li$_3$AlF$_6$ are present in a weight ratio LiF:Li$_3$AlF$_6$ ranging from about 11:24 to about 5:32.

24. An electrochemical probe according to claim 23, wherein said LiF:Li$_3$AlF$_6$ ratio is about 3:17.

25. An electrochemical probe according to claim 23, wherein said reference material comprises about 20% Al, about 68% Li$_3$AlF$_6$ and about 12% LiF, expressed in percentage by weight.

26. An electrochemical probe according to claim 21, wherein said LiF and Li$_3$AlF$_6$ are present in a weight ratio LiF:Li$_3$AlF$_6$ ranging from about 20:9 to about 11:23.

27. An electrochemical probe according to claim 26, wherein said LiF:Li$_3$AlF$_6$ ratio is about 19:10.

28. An electrochemical probe according to claim 13, for the continuous monitoring of lithium at temperatures of about 710° to about 770° C., wherein said reference material comprises Al, Li$_3$AlF$_6$ and AlF$_3$.

29. An electrochemical probe according to claim 28, wherein said β-alumina is sodium β-alumina.

30. An electrochemical probe according to claim 28, wherein said AlF$_3$ and Li$_3$AlF$_6$ are present in a weight ratio AlF$_3$:Li$_3$AlF$_6$ ranging from about 6:38 to about 12:35.

31. An electrochemical probe according to claim 30, wherein said AlF$_3$:Li$_3$AlF$_6$ ratio is about 7:37.

32. An electrochemical probe according to claim 13, for the continuous monitoring of a NaF/AlF$_3$ ratio at a temperature of about 950° C., wherein said reference material comprises Al and Na$_3$AlF$_6$ in admixture with NaF or Na$_5$Al$_3$F$_{14}$.

33. An electrochemical probe according to claim 32, wherein said reference material comprises Al together with Na$_3$AlF$_6$ and NaF in a weight ratio NaF:Na$_3$AlF$_6$ ranging from about 17:31 to about 2:50.

34. An electrochemical probe according to claim 33, wherein said NaF:Na$_3$AlF$_6$ ratio is about 5:46.

35. An electrochemical probe according to claim 32, wherein said reference material comprises Al together with $Na_3AlF_6$ and $Na_5Al_3F_{14}$ in a weight ratio $Na_5Al_3F_{14}:Na_3AlF_6$ ranging from about 9:44 to 37:19.

36. An electrochemical probe according to claim 35, wherein said $Na_5Al_3F_{14}:Na_3AlF_6$ ratio is about 18:36.

37. An electrochemical probe according to claim 12, wherein the electrode in contact with said reference material is made of stainless steel.

38. An electrochemical probe according to claim 12, wherein said monovalent metal in said molten substance and said further monovalent metal are identical.

* * * * *